United States Patent [19]
Madaras

[11] Patent Number: 5,483,571
[45] Date of Patent: Jan. 9, 1996

[54] RADIOGRAPHIC MOIRE

[75] Inventor: Eric I. Madaras, Yorktown, Va.

[73] Assignee: The United States of America as represented by the Administrator of the National Aeronautics and Space Administration, Washington, D.C.

[21] Appl. No.: 251,434

[22] Filed: May 31, 1994

[51] Int. Cl.⁶ .................................................. G21K 1/00
[52] U.S. Cl. ............................................ 378/145; 378/58
[58] Field of Search ............................... 378/145, 62, 58

[56] References Cited

U.S. PATENT DOCUMENTS 3,621,246  11/1971  Horsey .
3,728,542  4/1973  Golfier .
4,688,240  8/1987  Hosemann et al. .
5,125,016  6/1992  Korhonen et al. .
5,432,349  7/1995  Wood et al. ............................... 378/43

*Primary Examiner*—Craig E. Church
*Attorney, Agent, or Firm*—George F. Helfrich; Robert C. F. Perez

[57] ABSTRACT

A method for the x-ray inspection of materials making use of the Moire effect is described. The Moire effect results when two patterns are superimposed, a third pattern is produced. Any change in either of the first two patterns creates a change in the third. Moire inspection is common with visible light, this invention allows the technique to be extended to locations inaccessible to visual inspection. A first pattern of high radio contrast material is attached to or included in the sample. X-rays are projected through the sample. A second pattern is imposed at the observation point, either before or after the formation of the x-ray image. The two patterns interact to create a third, Moire, pattern. As the material is stressed the Moire pattern changes, the degree of change indicating the degree of stress.

14 Claims, 3 Drawing Sheets

RADIOGRAPHIC MOIRE

ORIGIN OF THE INVENTION

The invention described herein was made by an employee of the United States Government and may be manufactured and used by or for the Government for governmental purposes without the payment of any royalties thereon or therefor.

BACKGROUND OF THE INVENTION

1. Field of the Invention

The invention relates to the field of x-ray inspection, more particularly to x-ray inspection of macroscopic phenomena such as stresses in a material.

2. Description of the Related Art

Moire inspection is widely known in use for inspection of areas accessible to visible light. X-rays are widely known for use in observation of areas that cannot be penetrated by visible light. Numerous methods for examining strain are available including electronic and optical strain gages and optical methods such as holography, shearography and speckle interferometry. The present invention allows for the inspection of areas that cannot be observed with optical methods. The interior of materials that are not transparent to visible light cannot be observed with the optical methods enumerated above.

Strain gages have two large limitations, the first is that they monitor only a single point, the second is the need for cables running from the gage to its accompanying electronics. It is sometimes impractical when examining the interior of structures to have cables leading from the interior to the exterior. It would be difficult to prevent leakage from a high pressure tire, for example, if there were a cable running from its interior. The first limitation can be overcome by constructing the pattern of this method such that it covers a large area of the inspected object. The second is overcome as the remote nature of this method allows for the elimination of any such cables, There are some systems that make use of both x-rays and the Moire effect in diffraction measurements. These make use of reflection patterns to make measurements at the surface of a material. They are useful mostly on a very small scale and again fail to allow measurements at remote locations. The claimed method allows for remote measurements and large scale investigations.

SUMMARY OF THE INVENTION

The present invention is a method for using x-rays and the Moire effect to characterize materials. Its advantage lies in its use with materials that are substantially opaque to visible light, or interior regions that are not accessible making visible light Moire techniques unusable.

The first step involves attaching a first pattern to the material being inspected. By attaching is meant the process of attaching to the exterior, embedding within the material, or using a pattern already extant in the material. This could include the belting of a radial tire or a pattern of metal dots fastened to or embedded in a specimen. A pattern could also be attached first to an intermediate object that would in turn be attached to a specimen to be tested. The pattern used as the first pattern should be chosen to provide a radio opacity contrast of at least 2:1 with respect to the material being inspected. Alternatively the pattern could provide a radio opacity contrast of less than 2:1 and the resulting image could be enhanced using signal processing techniques.

To produce a Moire pattern a second pattern is necessary. This second pattern could be produced in a number of ways. It may be imposed over the detector so that the detected image already contains the Moire pattern. It could alternatively be imposed after the detecting step, for example by digitally scanning a film image into a computer, the line density of the digital scanner providing the second pattern.

The nature of the two patterns need not be important, any two patterns are capable of producing a Moire pattern, however for them to be useful in making quantitative measurements it is preferable that they be regular, for example, sets of substantially parallel lines with substantially constant separation distances. In addition, it is well known in the art that the geometry of an x-ray set up limits the resolution of that system. It is beneficial to detect an image as close as possible to the object being imaged. The size of the pattern elements and the sizes of their images will in turn govern the final resolution of the data produced through the present method. That is, a pattern of thin wires will be able to produce an image that will provide more detailed information than one of very thick wires.

Both of the patterns could be attached to the material being inspected. If the patterns were attached at different depths, for example the first at the surface and the second within the material, this would allow observation of differential motions within the material.

The images produced are created by x-radiation. X-radiation's penetrative character allows for characterization of areas that are inaccessible. The x-radiation should be beamed through the area of the material containing the first pattern and may be detected by any means. Film is an inexpensive detecting means and thus it lends itself to this method. It would be advantageous to make use of real time x-ray detecting methods to save the time necessary to develop film as well as reduce sample irradiation time. Digital real time radiography systems are capable of directly transferring detected images to a computer, by controlling the density of the imaging the Moire image can be produced and stored directly. Dynamic or flash x-ray systems are capable of even faster imaging that would allow dynamic measurements to be made and very short x-ray exposure times.

DESCRIPTION OF THE PREFERRED EMBODIMENTS

To produce a radiographic Moire pattern that is capable of demonstrating stress and other deformations in a rectangular matrix of RTV® rubber the present invention has been implemented in the following manner.

Figure 1:
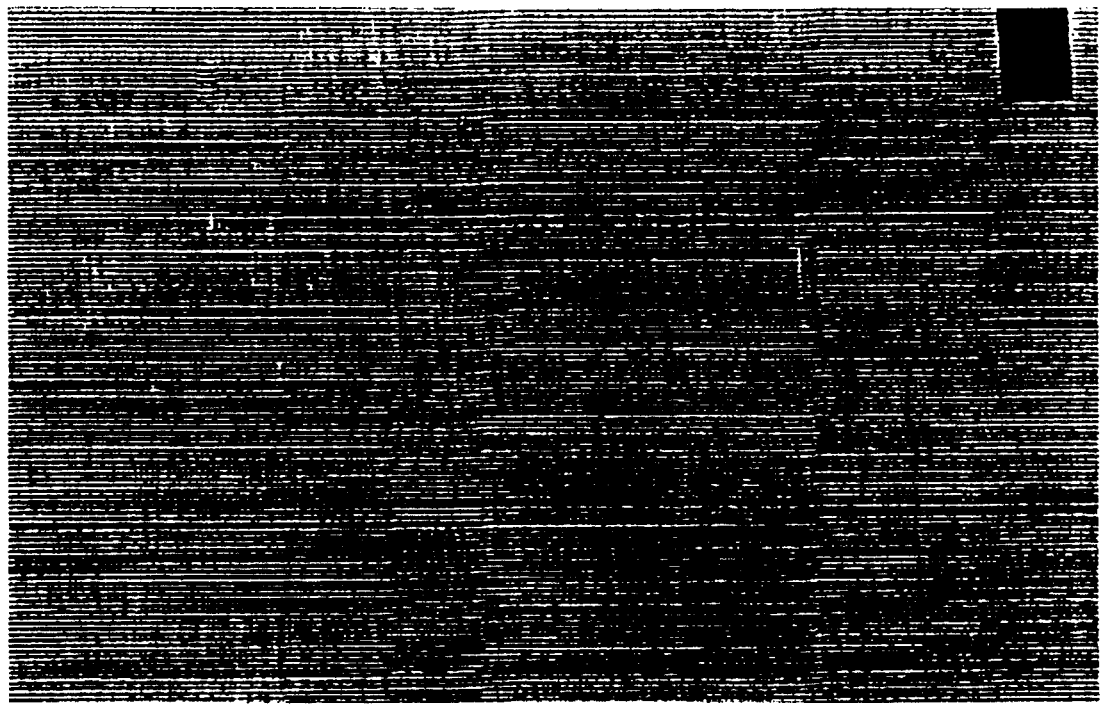
FIG. 1 is a drawing prepared from an x-ray photo of a test object used to implement the invention, an RTV® (GE Polymer Division) rubber matrix with a grid of 0.005" diameter steel wires attached and spaced 0.020" apart.

The first pattern as set out in the claims was in the form of a series of 0.005" diameter steel wires that were fixed to the matrix of RTV® rubber. Each wire was placed 0.020" from its neighbor and substantially parallel. An x-ray photograph of this wire plus rubber test piece is shown in FIG. 1 (note that in the test piece four wire positions were unintentionally crossed, causing the two dark bands).

Figure 2:
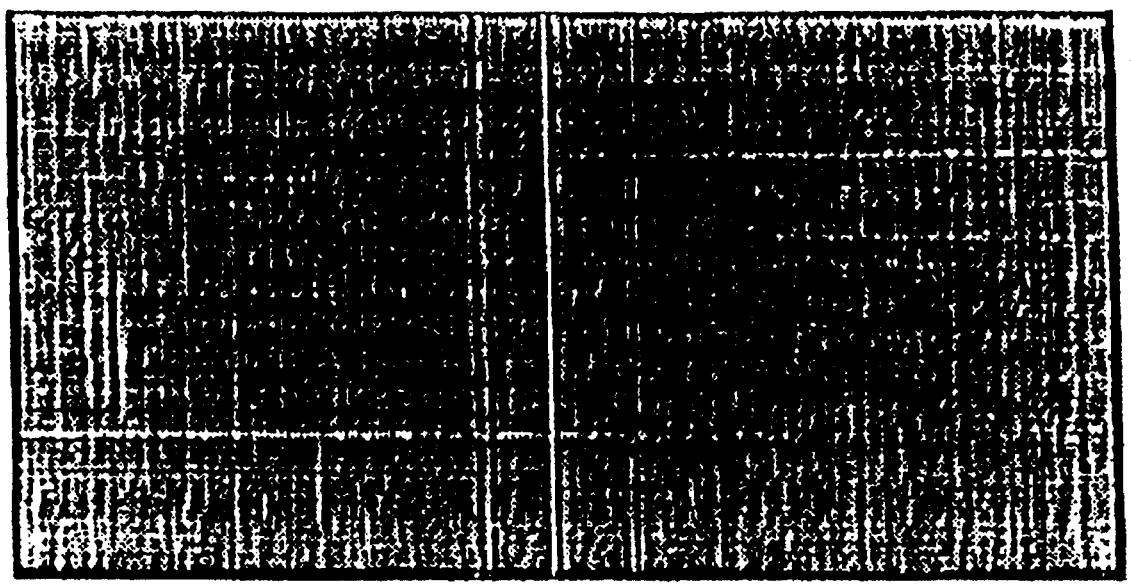
FIG. 2 is a drawing prepared from a computer image created by digitally scanning an x-ray photo into a computer. The image represents the Moire pattern produced by the test object of FIG. 1 as the object is bent around a cylinder 8" in diameter.
Figure 3C:
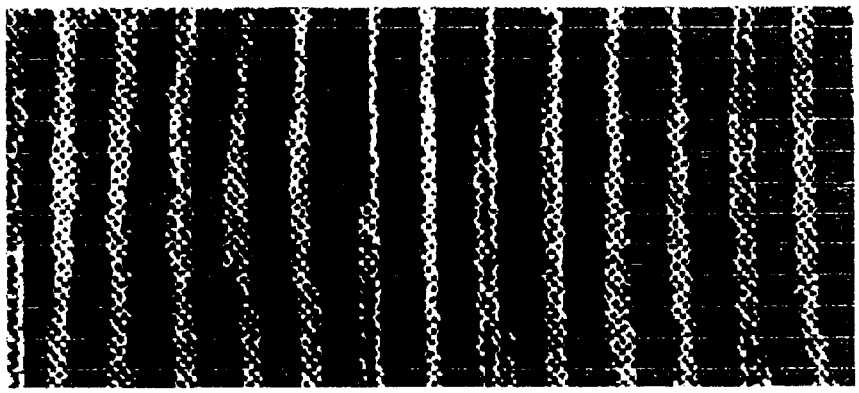
FIG. 3 is a drawing prepared from a computer image created by digitally scanning x-ray photos into a computer. Each of the three images represents the Moire pattern produced by the test object of FIG. 1 when a particular tensile load is applied. The first represents zero load, the second is a 5 lb. load and the third is a 10 lb. load.
Figure 3B:
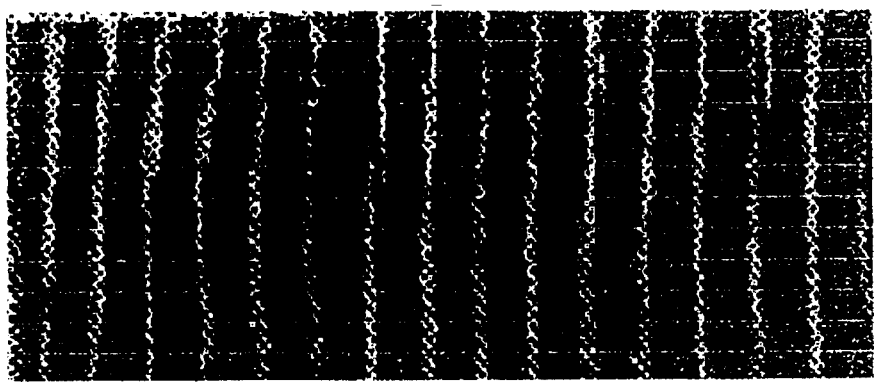
Figure 3A:
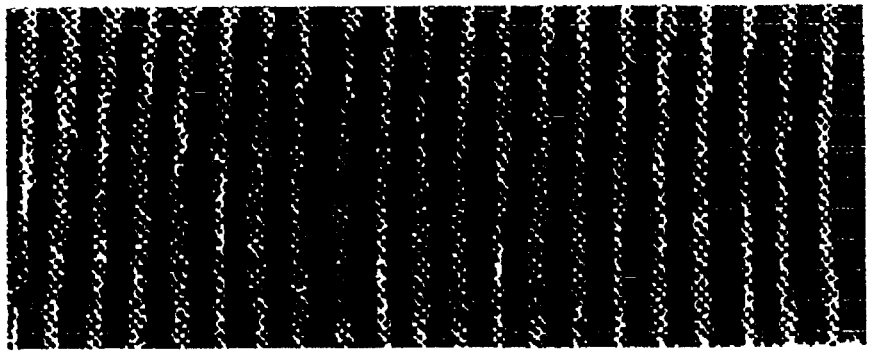

The test piece underwent various deformations including inducing a curvature of diameter 8", and applying a tensile load of zero, 5 lb. and 10 lb. An x-ray image was produced on film for each instance. These images were then digitally scanned into a computer. The line resolution of the digital scanning provided the second pattern necessary to produce a Moire pattern. The resulting Moire patterns are shown in FIGS. 2 and 3 respectively.

Another preferred embodiment is to use a series of metal dots in place of parallel wires. In measuring material properties it is desirable not to include the properties of the device used for measuring. By the substitution of dots the tensile properties of the wires are eliminated from any measurements.

Another preferred embodiment is to make use of existing patterns contained in the workpiece such as the belts of a tire.

Another preferred embodiment is to make use of real time radiography to produce images quickly, eliminating the film stage. Further, with proper setting of the resolution the digital display will act as the second pattern and the Moire image will be captured directly.

Another preferred embodiment is to make use of a flash x-ray or dynamic radiography system. This operates at a higher rate of speed than real time radiography and could be used to make measurements on a specimen under dynamic loads.

Another preferred embodiment is to attach both the first and second patterns to the material being inspected. This allows observation of the motions of two different depths of the material to be made so that differential movements can be quantified.

I claim:

1. A method of inspecting materials that are substantially opaque to visible light, which comprises:
   (a) attaching a first pattern to an area of a material being inspected, said first pattern being chosen to provide a radio opacity contrast of at least 2:1 with respect to the material being inspected;
   (b) producing a second pattern at a detecting means;
   (c) projecting x-radiation through the area of the material containing said first pattern;
   (d) detecting an image resulting from the passage of the x-radiation through the area of the material containing said first pattern;
   (e) observing a Moire pattern resulting from a combination of the first and second patterns.

2. A method of inspecting materials that are substantially opaque to visible light, which comprises:
   (a) attaching a first pattern to an area of a material being inspected, said first pattern being chosen to provide a radio opacity contrast of at least 2:1 with respect to the material being inspected, said first pattern consisting of an array of dots;
   (b) producing a second pattern at a detecting means, said second pattern consisting of substantially parallel lines;
   (c) projecting x-radiation through the area of the material containing said first pattern;
   (d) detecting an image resulting from the passage of the x-radiation through the area of the material containing said first pattern;
   (e) observing a Moire pattern resulting from a combination of the first and second patterns.

3. A method as recited in claim 2, wherein the dots are arranged into substantially parallel lines.

4. A method as recited in claim 2, wherein the dots are metal.

5. A method as recited in claim 2, wherein the second pattern is produced by digitally scanning the x-ray image, the digital nature of the scanning providing the second pattern of substantially parallel lines.

6. A method as recited in claim 1, wherein the image is observed using a real time radiography system.

7. A method as recited in claim 6, wherein the real time radiography system is digital and the second pattern is produced by the digital nature of the real time radiography system.

8. A method as recited in claim 2, wherein the image is observed using a real time radiography system.

9. A method as recited in claim 8, wherein the real time radiography system is digital and the second pattern is produced by the digital nature of the real time radiography system.

10. A method as recited in claim 1, wherein the image is observed with a dynamic radiography system.

11. A method as recited in claim 2, wherein the image is observed with a dynamic radiography system.

12. A method as recited in claim 1, wherein the radio opacity contrast is less than 2:1 and the image is enhanced using signal processing techniques.

13. A method as recited in claim 2, wherein the radio opacity contrast is less than 2:1 and the image is enhanced using signal processing techniques.

14. A method as recited in claim 1, wherein the second pattern is attached to the material being inspected, said second pattern chosen to provide a radio opacity contrast of at least 2:1 with respect to the material being inspected.

* * * * *